United States Patent [19]

Lu et al.

[11] Patent Number: 5,476,486
[45] Date of Patent: Dec. 19, 1995

[54] AUTOMATIC ATRIAL PACING PULSE THRESHOLD DETERMINATION UTILIZING AN EXTERNAL PROGRAMMER AND A V-SENSE ELECTRODE

[75] Inventors: Richard M. T. Lu, Highlands Ranch; Bruce M. Steinhaus, Parker; Peter A. Crosby, Greenwood Village, all of Colo.

[73] Assignee: Telectronics Pacing Systems, Inc., Englewood, Colo.

[21] Appl. No.: 205,795

[22] Filed: Mar. 4, 1994

[51] Int. Cl.⁶ .................................................. A61N 1/36
[52] U.S. Cl. .................................. 607/28; 128/695 R
[58] Field of Search ............................ 607/9, 11, 27, 607/28

[56] References Cited

U.S. PATENT DOCUMENTS

| | | | |
|---|---|---|---|
| 3,777,762 | 12/1973 | Nielsen | 607/28 |
| 3,949,758 | 4/1976 | Jirak | 607/28 |
| 4,674,508 | 6/1987 | De Cote | 607/28 |
| 4,817,605 | 4/1989 | Sholder | 607/28 |
| 4,903,700 | 2/1990 | Whigham et al. | 128/419 |
| 4,969,462 | 11/1990 | Callaghan et al. | 128/419 |
| 5,172,690 | 12/1992 | Nappholz et al. | 128/419 |
| 5,265,603 | 11/1993 | Hudrlik | 607/28 |

Primary Examiner—George Manuel
Assistant Examiner—Marianne Parker
Attorney, Agent, or Firm—Gottlieb, Rackman & Reisman

[57] ABSTRACT

A clinical programming system is disclosed for use with an implanted cardiac pacemaker to automatically determine the minimum pacing energy which is necessary to evoke an atrial depolarization. The system utilizes a series of pacing pulses of progressively decreasing energies to stimulate the atrium and detects following R-waves. The absence of an R-wave indicates the loss of atrial capture.

15 Claims, 2 Drawing Sheets

AUTOMATIC ATRIAL PACING PULSE THRESHOLD DETERMINATION UTILIZING AN EXTERNAL PROGRAMMER AND A V-SENSE ELECTRODE

FIELD OF THE INVENTION

This invention relates to implantable pulse generators or other medical devices, including tachycardia reversion devices and defibrillators, and more particularly to determining the minimum pacing energy to "capture" the atrial chambers of a patient's heart, i.e., to cause an atrial contraction.

BACKGROUND OF THE INVENTION

The atrial or ventricular pacing threshold is the minimum pulse energy (usually expressed as a voltage of a fixed width pulse) required to stimulate the muscle cells of the atria or ventricles to depolarize, i.e., to contract.

Pacing thresholds must be determined when the pacemaker, or other therapeutic pulse generator, is first implanted in the patient, and during subsequent follow-up examinations, to ensure that reliable "capture" is obtained while expending minimum energy. This is important since the pacemaker is battery powered and has a limited life. A conventional battery, depending on mode of operation, lead impedance, pulse amplitude, pacing rate and pulse width, may have a longevity typically ranging from four to ten years. Pulse amplitude and pulse width (which translate into energy consumed) are important factors in battery life.

Both the atrial and ventricular pacing thresholds must be measured if a dual chamber device is implanted. If a ventricular single-chamber device is implanted, then only the ventricular pacing threshold is required. If an atrial single-chamber device is implanted, then only the atrial pacing threshold is required. After a pacing threshold is measured, an appropriate pacing energy is chosen and programmed for the implanted pulse generator. The pacing energy is conventionally chosen to be two or three times the measured threshold so as to allow a safety margin for reliable capture.

Thresholds are measured at the time of implant with a pacing system analyzer when direct electrical access to the leads is possible. After implant, when the leads are not accessible, another method must be used. Conventionally, the threshold test is done with the aid of a programmer, which communicates with the implanted pulse generator via a telemetric link, at the same time that the patient's surface electrocardiogram (ECG) is viewed. Conventionally, either the atrial or ventricular threshold test starts from the previously programmed pulse amplitude and pulse width. The test is performed by automatically and progressively decreasing the pacing pulse amplitude by a fixed percent (e.g., 6%) on each test pace. The percent of decrease varies with the impedance of the lead involved. The pacing rate during the threshold test is set at a rate just above the patient's intrinsic rate to ensure that the pacing pulses will capture the heart.

When an atrial threshold is being measured, the amplitude of each decreased amplitude pulse can be annotated on the surface ECG trace. The amplitude of the last pulse to capture the heart represents the "pacing threshold." All pulses are delivered at the last programmed pulse width and pacing polarity. Unless halted manually, the test continues until either the pulse amplitude falls to a minimum predetermined voltage, or a fixed number of decreased amplitude pulses have been delivered.

The operator visually decides from the surface ECG when a loss of capture occurs, and thereupon manually terminates the test. The programmer displays the amplitude of the next-to-last pacing pulse before the termination of the test. If the test was not terminated immediately after that pulse which lost capture, the displayed amplitude will not be the true pacing pulse threshold. Therefore, the pacing pulse threshold must be confirmed by the operator by visual examination of the surface ECG. If the ECG trace is on paper, that portion of the ECG where a loss of capture occurred can be examined. If the ECG provides a trace into only a limited window of storage, then that portion of interest in the ECG may or may not be available, and the test may have to be done again. Thus, the conventional test procedure may be very time consuming. Pacing pulse thresholds also may not be determined appropriately due to operator error and this may have safety consequences for the patient.

In U.S. Pat. No. 4,969,462, issued Nov. 13, 1990 to F. J. Callaghan et al., for "Pacemaker With Improved Automatic Output Regulation", there is disclosed a threshold search by an implantable pacemaker which determines the pacing threshold by sensing the evoked potentials which follow the pacing stimuli and automatically sets the values of pacing energy accordingly. The pacing pulse is delivered between the tip electrode located inside the heart and the case of the pacemaker which is located under the skin on the patient. Sensing for evoked potentials is performed between the ring electrode located in the heart and the case. But in many patients only a unipolar lead, one with a tip electrode but no ring electrode, is available, and therefore pacing and sensing must be done through the same tip and case electrodes. In such a case, measurement of the capture threshold may not be feasible, because the pacing pulse induces potentials in the immediate area of the heart which are very much greater than those resulting from a heartbeat. Until the charges resulting from the pacing pulse dissipate sufficiently, reliable sensing is impossible.

To permit sensing with the same electrodes which are used for pacing, a triphasic stimulation waveform has been described by Whigham et al. in U.S. Pat. No. 4,903,700, issued Feb. 27, 1990, for "Pacing Pulse Compensation". Here the first and third phases of the pacing pulse are of one polarity and the second phase is of the other polarity, so that the net charge to the heart muscle is zero. This allows the same electrode which conducted the pacing pulse to sense the evoked potential. Due to the different surface treatments of pacing electrodes, the procedures described by Nappholz et al. in U.S. Pat. No. 5,172,690, issued Dec. 22, 1992 for "Automatic Stimulus Artifact Reduction For Accurate Analysis of the Heart's Stimulated Response", are advantageously incorporated to optimally adjust the triphasic waveform to reduce the stimulus polarization artifact. However, optimal triphasic waveforms may still be difficult to obtain with electrodes which have very high polarization characteristics.

Moreover, when pacing threshold searches are done routinely by the pacemaker, as described by Callaghan et al. and Nappholz et al., they may unnecessarily consume energy and shorten the life of the battery of the pacemaker due to the energy required to run the threshold searches. This is especially true today with the availability of drug-eluting leads which provide low and stable pacing thresholds.

SUMMARY OF THE INVENTION

A conventional clinical programmer with an innovative mode of operation is utilized during the implantation, and the follow-up examination, of a pacemaker to automatically determine the atrial pacing threshold of a patient with satisfactory AV conduction. To avoid occurrences of competition or fusion beats, or both, the pacing is done at a faster than normal rate, and in the DDD mode instead of the conventional DOO mode. It is assumed that the patient has adequate atrioventricular conduction. A telemetry link provides from the pacemaker to the programmer main timing events corresponding to the A-pace and the V-sense in a cardiac cycle. Capture of the atria by the A-pace is indicated by a corresponding V-sense in the ventricles within an appropriate atrioventricular delay window. Correspondingly, lack of capture of the atria by the A-pace is indicated by the absence of a corresponding V-sense in the ventricles during a window of time following an atrioventricular delay.

This automatic threshold test provides more consistently accurate pacing threshold measurements, improved ease of use of the programmer, and saving of operator time. The method can also be implemented in an implanted device for automatic atrial threshold testing, preferably with infrequent execution.

DESCRIPTION OF THE DRAWINGS

Further features and advantages of this invention will become apparent upon consideration of the following detailed description in conjunction with the drawing, in which.

DESCRIPTION OF THE INVENTION

Figure 1:
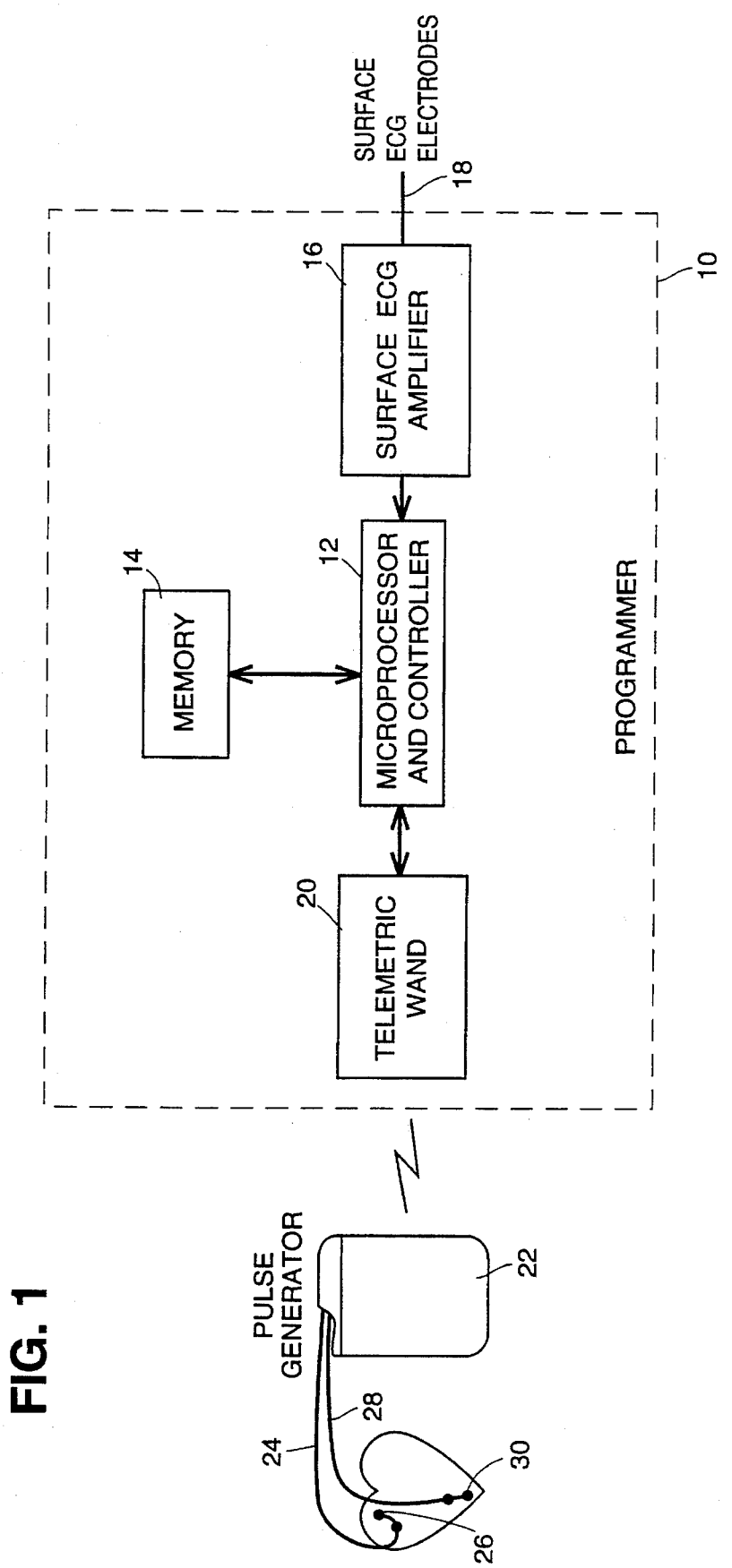
FIG. 1 is a block diagram of the hardware system of the invention including a programmer and an implanted pulse generator.

The hardware system shown in FIG. 1 comprises a programmer 10, which includes a microprocessor and controller 12, a memory 14, a surface electrocardiographic amplifier 16 having a patient cable 18 with surface ECG electrodes (not shown), and a telemetric wand 20. A pulse generator 22 (pacemaker) is implanted in the patient and is here shown as having an atrial lead 24 with an electrode 26 located adjacent to the muscle wall of the right atrium, and a ventricular lead 28 with an electrode 30 located adjacent to the muscle wall of the right ventricle. An exemplary programmer is the 9600 Network Programmer, manufactured by Telectronics Pacing Systems, Inc., which is a combined programmer/ECG monitor and recorder and has several replaceable memory cassettes which contain the operating software and data storage memory required for different pacemakers. An exemplary pulse generator is the META DDDR Model 1254 dual chamber, rate responsive, multiprogrammable, cardiac pulse generator with telemetry and a range of functions which includes fourteen pacing modes. An exemplary atrial lead is a Telectronics Accufix Model 330-801.

The innovative test procedure is initiated by pressing an appropriate key on the programmer to cause a command, via a telemetric link which includes the programmer wand 20 and a telemetry transceiver in the pulse generator, to be issued to the pulse generator to deliver a test pacing pulse sequence to the heart, at a pacing rate which is usually higher than the programmed standby rate (e.g., 100 pulses per minute), in an inhibition mode which is DDD for an atrial test. The atrial threshold test is performed by progressively decreasing the amplitudes of successive atrial pacing pulses in the sequence by either a certain percentage (e.g., 6%) or a certain voltage (e.g., 0.2 v) for each pulse. [Alternatively, the pulse width may be progressively reduced, or a combination of amplitude and width may be reduced.] Following the delivery of each test pacing pulse, signals are transmitted telemetrically by the pulse generator to the programmer which are main timing events for capture classification.

Figure 2:
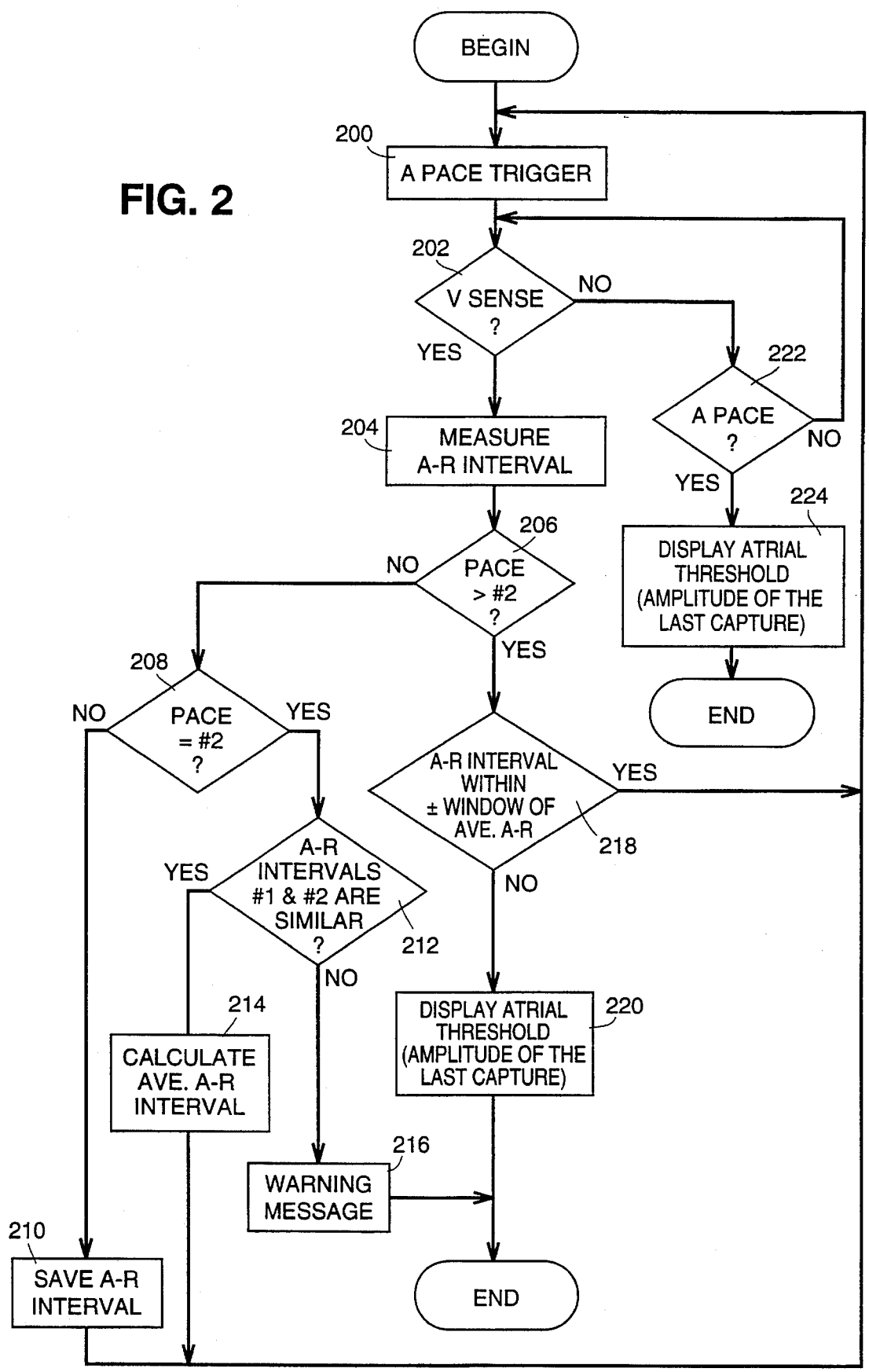
FIG. 2 is a flow chart of the algorithm utilized in the system of FIG. 1 to automatically determine the atrial threshold value from ventricular senses.

FIG. 2 shows the logic diagram for determining the atrial capture threshold by generating atrial pacing pulses and monitoring respective ventricular responses. This method requires the patient to possess atrioventricular conduction, so that a P-wave in the atrial muscle is conducted to the ventricular muscle. To allow as long a time as possible for a spontaneous ventricular beat, the AV delay is programmed preferably to a long interval, e.g., 300 milliseconds, for the test procedure.

The A-pace trigger of step 200 enables V-sensing in step 202. If there is an A-pace, and subsequently there is a V-sense within an extended A-V delay window, then the A-R interval is measured in step 204. In step 206, a check is made whether at least two A-paces have already been generated. If not, then in step 208 a determination is made whether the current A-pace is the second. If not, then it must be the first and in step 210 the measurement of the A-R interval is stored and the system waits for the next A-pace. But if it is the second, then in step 212 a comparison is made whether the first two A-R intervals were similar, e.g., within ±50 ms. If they were similar, then in step 214 their average is taken and the system waits for the next A-pace. If the A-R intervals are determined to be not similar in step 210, then in step 216 the system delivers a warning message, and ends the procedure.

If in step 206 it is determined that the current A-pace is the third or higher A-pace in the series, then in step 218 a check is made whether the A-R interval is within a window around the average A-R interval as previously determined in step 214. If the current A-R interval is within ±50 ms of the average A-V interval, then the A-pace is classified as having captured the atria, and the system waits for the next A-pace. But if the current A-R interval does not fall within the ±50 ms window around the average A-R interval, then the A-pace is classified as having been a non-capture pulse, and in step 220 the amplitude of the last A-pace that effected capture is displayed and the procedure is ended.

Returning now to the V-sense step 202, so long as there is no V-sense, in step 222 the system checks for an A-pace. If there is an A-pace, and there is no V-sense in step 202 to enable the A-R interval measurement in step 204, then in step 224 the amplitude of the last A-pace that effected capture is displayed, and the procedure is ended.

It will be appreciated that the arrangement of pacing in the atrium and sensing in the ventricle completely avoids the need to engage in triphasic balancing of the pacing electrode.

Instead of using telemetered main timing events, a similar test can be performed by utilizing the R-wave appearing in the ECG surface waveform as an indication of a capture A-pace which gave rise to a ventricular beat. Similarly, telemetering the intracardiac electrogram can be substituted for telemetering main timing events. Also, telemetry is not needed if the processing is done inside the implanted pacemaker.

The test is considered complete when a single A-R interval falls outside the window around the average. The A-R intervals are sufficiently consistent that a single departure evidences loss of capture. However, it is possible to employ an X out of Y procedure, e.g., only if two of the last three A-R intervals fall outside the window is it concluded that there has been a loss of capture. Similar remarks apply to how many A-paces occur without preceding V-senses before it is determined that a loss of capture has occurred.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

What is claimed is:

1. A method of determining a minimum energy of a pacing pulse necessary to evoke an atrial depolarization response in a heart of a patient, comprising the steps of:

generating a series of test atrial pacing pulses, each pulse having sequentially decreasing energy;

verifying an occurrence of a ventricular beat within a predetermined interval following each generated test atrial pacing pulse; and determining said minimum energy as a function of the energy of the last test atrial pacing pulse which resulted in the occurrence of a ventricular beat within said predetermined interval.

2. A method according to claim 1 further comprising implanting in said patient a sensor for sensing ventricular beats, said pulse sensor including a telemetry circuit, wherein said verifying step is carried out by detecting a telemetric signal from said telemetry circuit.

3. A method according to claim 1 further comprising the step of obtaining a surface electrocardiogram, wherein said verifying step is carried out by analyzing said surface electrocardiogram.

4. A method according to claim 3 further including the steps of:

measuring time intervals between a number of a first test atrial pacing pulses and respective following ventricular beats and, if they are similar, then forming an average of such time intervals; and verifying an occurrence of a subsequent ventricular beat only if said subsequent ventricular beat follows a preceding test atrial pacing pulse within a predetermined time window around said average.

5. A method according to claim 2 further including the steps of:

measuring time intervals between a number of a first test atrial pacing pulses and respective following ventricular beats and, if they are similar, then forming an average of such time intervals; and verifying an occurrence of a subsequent ventricular beat only if said subsequent ventricular beat follows a preceding test atrial pacing pulse within a predetermined time window around said average.

6. A method according to claim 1 further including the steps of:

measuring time intervals between a number of first test atrial pacing pulses and respective following ventricular beats and, if they are similar, then forming an average of such time intervals; and verifying an occurrence of a subsequent ventricular beat only if said subsequent ventricular beat follows a preceding test atrial pacing pulse within a predetermined time window around said average.

7. Apparatus for determining a minimum energy of a pacing pulse necessary to evoke an atrial depolarization response in a heart of a patient, comprising:

means for generating a series of test atrial pacing pulses, each pulse having sequentially decreasing energy;

means for verifying an occurrence of a ventricular beat within a predetermined interval following each generated test atrial pacing pulse; and means for determining said minimum energy as a function of the energy of the last test atrial pacing pulse which resulted in the occurrence of a ventricular beat within said predetermined interval.

8. Apparatus according to claim 7 wherein said means for verifying includes means implanted in said patient for sensing ventricular beats, said implanted means including a telemetry circuit and means external of said patient for detecting a telemetric signal from said telemetry circuit.

9. Apparatus according to claim 7 further comprising means for obtaining a surface electrocardiogram indicative of ventricular beats, wherein said means for verifying includes means for analyzing said surface electrocardiogram.

10. Apparatus according to claim 9 further including means for measuring time intervals between a number of a first test atrial pacing pulses and respective following ventricular beats and, if they are similar, then forming an average of such time intervals; and wherein said verifying means verifies an occurrence of a subsequent ventricular beat only if said subsequent ventricular beat follows a preceding test atrial pacing pulse within a predetermined time window around said average.

11. Apparatus according to claim 10 wherein said window is within a range of plus and minus 50 milliseconds.

12. Apparatus according to claim 8 further including:

means for measuring time intervals between a number of a first test atrial pacing pulses and respective following ventricular beats and, if they are similar, then forming an average of such time intervals; and wherein said verifying means verifies an occurrence of a subsequent ventricular beat only if said subsequent ventricular beat follows a preceding test atrial pacing pulse within a predetermined time window around said average.

13. Apparatus according to claim 12 wherein said window is within a range of plus and minus 50 milliseconds.

14. Apparatus according to claim 7 further including:

means for measuring the time intervals between a number of a first test atrial pacing pulses and respective following ventricular beats and, if they are similar, then forming an average of such time intervals; and wherein said verifying means verifies an occurrence of a subsequent ventricular beat only if said subsequent ventricular beat follows a preceding test atrial pacing pulse within a predetermined time window around said average.

15. Apparatus according to claim 14 wherein said window is within a range of plus and minus 50 milliseconds.

* * * * *